United States Patent [19]

Thut et al.

[11] Patent Number: 5,505,922

[45] Date of Patent: Apr. 9, 1996

[54] ANESTHETIC PHARMACEUTICAL COMBINATION

[75] Inventors: Paul D. Thut; Michael D. Turner, both of Baltimore, Md.

[73] Assignee: University of Maryland at Baltimore, Baltimore, Md.

[21] Appl. No.: 394,049

[22] Filed: Feb. 24, 1995

Related U.S. Application Data

[63] Continuation of Ser. No. 105,567, Aug. 13, 1993, abandoned.

[51] Int. Cl.$^6$ .......................... A61K 33/14; A61K 33/00
[52] U.S. Cl. .......................... 424/677; 424/715; 424/722; 514/818
[58] Field of Search .......................... 424/10, 11; 514/220

[56] References Cited

U.S. PATENT DOCUMENTS

| | | | |
|---|---|---|---|
| 4,172,118 | 10/1979 | Baetz | 424/10 |
| 4,307,078 | 12/1981 | Nelson | 424/10 |
| 4,873,076 | 10/1989 | Fishman et al. | 424/10 |
| 5,013,539 | 5/1991 | Norris et al. | 424/10 |
| 5,061,477 | 10/1991 | Kappas et al. | 424/10 |

*Primary Examiner*—Werren B. Lone
*Attorney, Agent, or Firm*—Sughrue, Mion, Zinn, Macpeak & Seas

[57] ABSTRACT

An anesthetic pharmaceutical combination comprising the combination of a local anesthetic and lithium ions present in an amount effective to lower the amount of the local anesthetic necessary to achieve equivalent anesthetic effect in a patient and a method of use of the anesthetic pharmaceutical combination.

16 Claims, 3 Drawing Sheets

ANESTHETIC PHARMACEUTICAL COMBINATION

This is a Continuation of application Ser. No. 08/105,567 filed Aug. 13, 1993, abandoned.

FIELD OF THE INVENTION

The invention relates to an anesthetic pharmaceutical combination comprising lithium ions co-administered in the same local area with a local anesthetic and to a method of enhancing the anesthetic effect of a local anesthetic where the amount of the local anesthetic that is necessary to achieve a requisite anesthetic effect in a patient can be reduced by use of the lithium ions in combination.

BACKGROUND OF THE INVENTION

Local anesthetics are used in a wide variety of medical procedures. The situations where local anesthetics are used range from infiltrations to facilitate suturing lacerations in emergency rooms to prolonged use during reconstruction of hands or feet or as in tissue grafting following burns.

Local anesthetics are also used, in particular, during dental surgery, including procedures ranging from simple cavity repair to extraction and soft tissue procedures.

There are a number of local anesthetics that are used for various clinical purposes. Examples of such local anesthetics include lidocaine, bupivacaine, chloroprocaine, mepivacaine, procaine, tetracaine, and etidocaine.

These products vary in onset, duration and potency, however, the mode of action for local anesthetic drugs is essentially the same. More specifically, local anesthetics inhibit the inward flow of sodium ions in afferent small diameter C type nerve fibers, which carry certain types of pain sensations.

Local anesthetics are commonly administered using a sodium-containing buffer vehicle in order to maintain the pH and isotonicity of the anesthetic.

Unfortunately, as a result of the blockage of the sodium currents during action potential propagation caused by the local anesthetic, these anesthetic drugs may also exhibit toxicity in efferent somatic nerves, the heart, brain and other electrically excitable tissues (See Covino, B. G. "Toxicity and systemic effects of local anesthetic agents," Local Anesthetics (Strichartz, G. R. ed) *Handbook of Experimental Pharmacology*, Vol 81, Springer-Verlag, Berlin, 1987, pp 187–212, Garfield, J. M. and Gugino, L. "Central effects of local anesthetics." in Local Anesthetics, ibid. pp 253–284. and Munson, E. S. Mepivacaine overdose in a child *Anesth. Analg.* (Cleve, 52:422, 1973.) However, the potential toxicity of these anesthetic drugs is reduced when the molar dose of the local anesthetic can be minimized. (See Scott, D. B. et al..,: "Factors affecting plasma levels of lidocaine and prilocaine". *Br. J. Anaesh.* 44:1040, 1972.]

SUMMARY OF THE INVENTION

Accordingly, an object of the present invention is to reduce the potential toxicity of local anesthetics by minimizing the molar dose thereof without any substantial loss of anesthetic effectiveness.

An additional object of the present invention is to provide an anesthetic pharmaceutical combination enhancing the local anesthetic effect.

A further object of this invention is to provide a method of enhancing localized anesthetic effect thereby reducing the amount of local anesthetic needed for pain level reduction.

These and other objects of the present invention, which will be apparent from the detailed description of the present invention provided hereinafter, have been met by the anesthetic pharmaceutical combination and method of this invention.

More specifically, one embodiment of this invention provides an anesthetic pharmaceutical combination comprising (1) an anesthetic capable of providing localized anesthetic characteristics and (2) a liquid vehicle containing 10 to 90 mmolar lithium ions, preferably 30 to 70 mmolar lithium ions, as cations.

A further embodiment of this invention provides a method of enhancing localized anesthetic effects upon administration of a local anesthetic to a patient comprising administering to a patient an anaesthetic pharmaceutical combination comprising a local anaesthetic in combination with a liquid vehicle containing 10 to 90 mmolar of lithium ions, as preferably 30 to 70 mmolar lithium ions.

BRIEF DESCRIPTION OF THE DRAWINGS

In particular, FIG. 1 shows the mepivacaine probit/dose effect curve in 0% lithium Lockes buffer at $ED_{50}$, $ED_{90}$ and $ED_{95}$ for in vitro testing of ferret desheathed vagus C fibers. FIG. 2 shows the mepivacaine probit/dose effect curve in 35% lithium Lockes buffer at $ED_{50}$, $ED_{90}$ and $ED_{95}$ for in vitro testing of ferret desheathed vagus C fibers.

FIG. 3 shows the procaine probit/dose effect curve in 0% lithium Lockes buffer at $ED_{50}$, $ED_{90}$ and $ED_{95}$ for in vitro testing of ferret desheathed vagus C fibers. FIG. 4 shows the procaine probit/dose effect curve in 35% lithium Lockes buffer at $ED_{50}$, $ED_{90}$ and $ED_{95}$ for in vitro testing of ferret desheathed vagus C fibers.

FIG. 5 shows the mepivacaine probit/dose effect curve in 0% lithium Lockes buffer at $ED_{50}$, $ED_{90}$ and $ED_{95}$ for the in vivo testing of rabbit tooth pulp assay. FIG. 6 shows the mepivacaine probit/dose effect curve in 35% lithium Lockes buffer at $ED_{50}$, $ED_{90}$ and $ED_{95}$ for in vivo testing of rabbit tooth pulp assay.

DETAILED DESCRIPTION OF THE INVENTION

Figure 1:
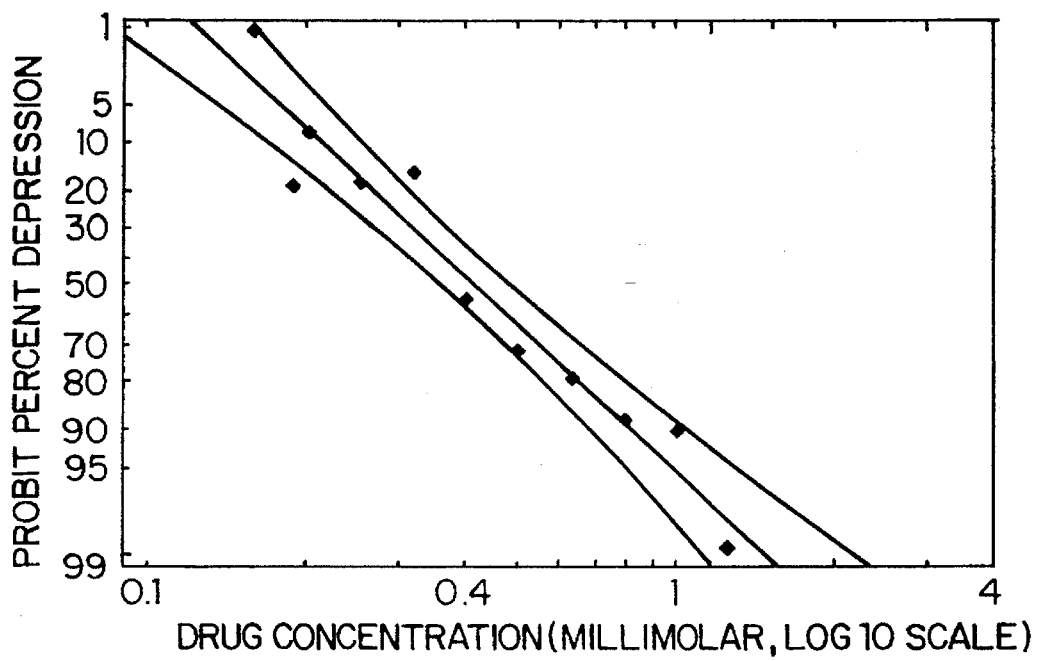
FIGS. 1–6 show the probit/Dose effect curves for various anesthetics in various buffers.
Figure 2:
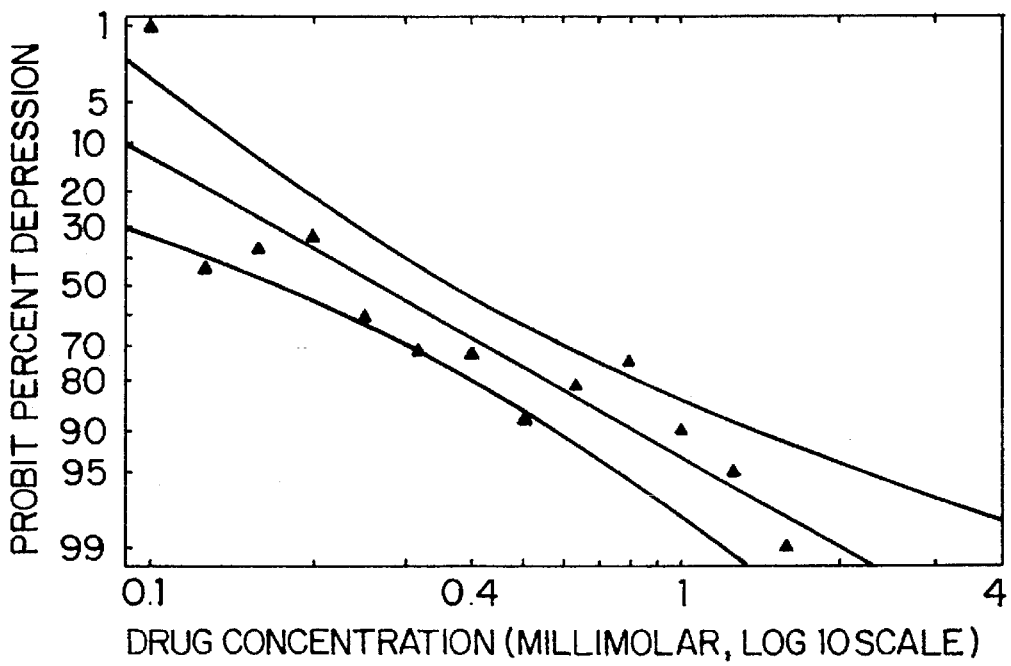
Figure 3:
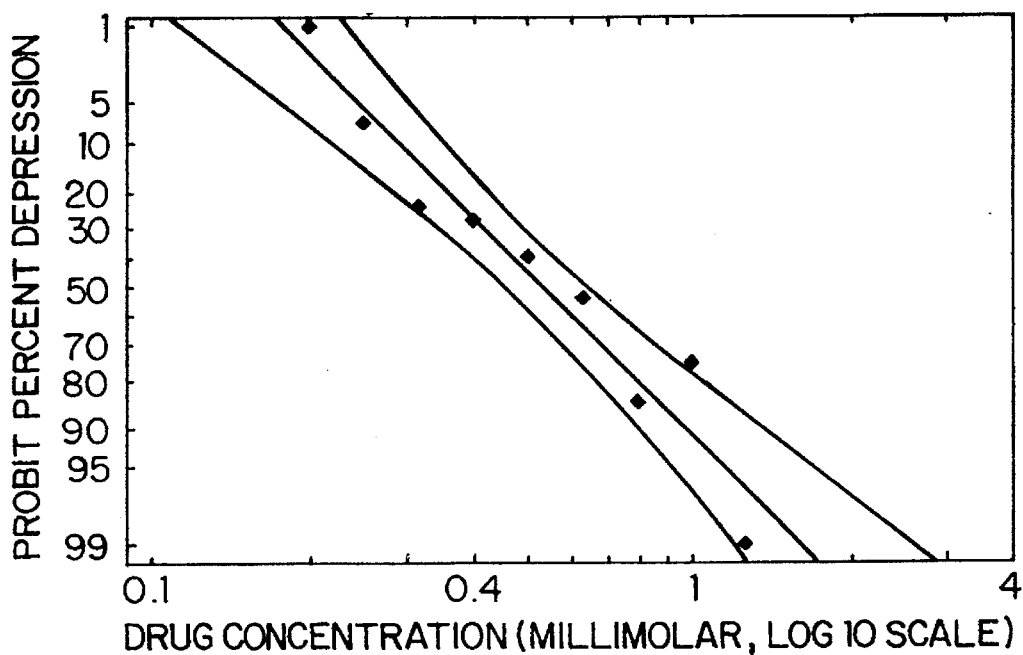
Figure 4:
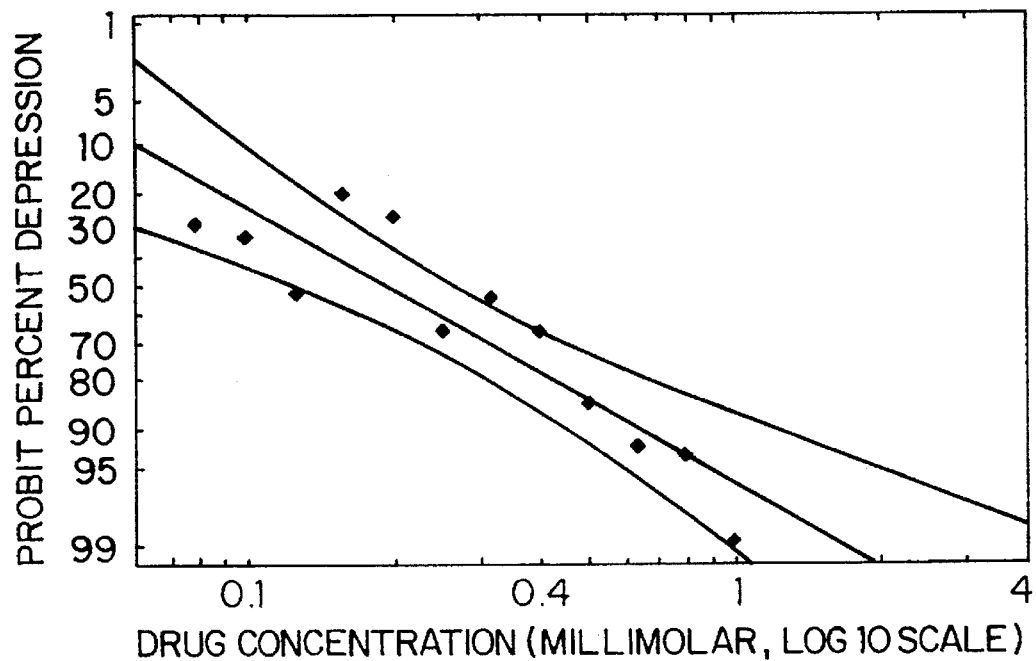

As discussed above, the mode of action for local anesthetics is through inhibiting the inward flow of sodium ions into nerves through cation channels.

Presently, local anesthetics are commonly co-administered in a sodium-containing buffer vehicle which is isotonic with typical body fluids and is buffered to provide appropriate anesthetic solubility. A typical sodium containing buffer is one containing 20.0 mg of lidocaine hydrochloride; 0.01 mg of epinephrine; 0.55 mg of sodium bisulfite; 6.0 mg of sodium chloride and sodium hydroxide for pH adjustment per ml. As a result, sodium ions are outside the nerve, and thus the dose of local anesthetic administered must be sufficient to overcome the effects of this increased concentration of sodium ions outside the nerve.

Unfortunately, the required level of local anesthetic which needs to be administered can result in toxicity in efferent somatic nerves, the heart, brain and other electrically excitable tissues. As a result, it is desired to provide techniques where equivalent pain sensation reduction can be achieved using a lower dosage of anesthetic.

As discussed above, an object of the present invention is to reduce the potential toxicity of local anesthetics by minimizing the molar dose necessary to obtain anesthetic effect in a subject. This object has been met by using lithium ions in a vehicle for the administration of local anesthetics. In a typical sodium ion containing buffer, sodium ions are replaced by lithium ions such that the lithium ion to sodium ion molar ratio is 2:1 to 1:2. To further explain a conventional sodium containing buffer is about 100 mmolar in sodium ions. Such a buffer modified in accordance with the principles of this invention would be to replace sodium cations with lithium cations such that the buffer ion concentration becomes 10 mol % to 60 mol % Li ions to 90 mol % to 40 mol % Na ions.

More specifically, lithium is a monovalent cation with a molecular size, including hydrating water molecules, which is larger than sodium. Thus, lithium ions can maintain the same transmembrane potential as sodium but they are less efficient in crossing the cation channel during propagation of the action potential.

Based on the above, the present inventors have determined that a vehicle generally used for injection, i.e., which is isotonic with body fluids and contains sodium ions, if sodium cations are replaced with lithium cations in the ratio as set forth above will reduce the required local anesthetic dosage, and thereby reducing the potential toxicity of these anesthetic drugs and achieving a substantially equivalent pain sensation reduction.

While it is known that toxic effects may be observed if blood levels of lithium exceed certain concentrations, this is not a concern in the present invention in terms of the amount of lithium which can be used to achieve the above objects of the present invention. That is, acutely, 250 mg per ml of lithium are known to be well tolerated. However, the lithium doses used in the present invention are many orders of magnitude lower than this amount, e.g., lithium is used in an amount to produce a level ranging from 0.0001 mEq/liter to 0.0009 mEq/liter, more preferably 0.0003 mEq/liter to 0.0007 mEq/liter.

As previously mentioned, examples of local anesthetics to which the present invention is applicable include: amide type local anesthetics, such as mepivacaine, lidocaine, mepivacaine, etidocaine and prilocaine; ester type local anesthetics, such as procaine, chloroprocaine, and tetracaine; and antihistamine-like anesthetics, such as benadryl. These anesthetics can be present in the anesthetic pharmaceutical combination alone or as a mixture of two or more thereof.

The lithium-containing buffer vehicles used in the combination of the present invention can be administered to the subject, e.g., mammals such as human and animal, using conventional techniques.

The anesthetic pharmaceutical combination of the present invention can be formulated as a physiologically acceptable injectate comprising an admixture of a local anesthetic and lithium ions. Alternatively, the anesthetic pharmaceutical combination can comprise separately a vehicle for ions, where these vehicles are used locally in combination to achieve the advantages of the present invention.

The anesthetically effective amount of the anesthetic administered with the lithium-containing vehicle of the present invention will vary depending upon, e.g., tissue pH, dosage frequency, degree of vascularization, whether a vasoconstrictor is also used, and the like. Commonly, local anesthetics are formulated as 0.5 wt % to 5.0 wt % solutions and are administered conventionally within this concentration range.

Consequently, the concentration of lithium ions in the vehicles used in the present invention necessary to lower the anesthetically effective dose of a local anesthetic will likewise vary depending upon such factors and can be easily determined by one skilled in the art using routine experimentation.

As described above, the anesthetic pharmaceutical combination of this invention comprises an anesthetic providing localized anesthetic effects in combination with lithium ions as cations in an amount effective to provide an enhancement of and reduction in toxicity of the effects of the local anesthetic. The combination can comprise a physiologically acceptable vehicle containing the local anesthetic and the lithium ions in admixture in water as the liquid or can comprise separately prepared physiologically acceptable vehicles, one containing the local anesthetic and the other the lithium ions each vehicle containing water as the liquid component, for use in combination to achieve the advantages of the present invention. In addition to the anesthetic and the lithium ions as active components, the vehicle employed can additionally include physiologically acceptable components such as sodium chloride and like materials conventionally used to achieve isotonicity with typical body fluids, pH buffers to establish a physiologically compatible pH range and to enhance the solubility of the anesthetic present, vasoconstrictors such as epinephrine, preservatives, stabilizers and antioxidants and the like. In general, any physiologically acceptable component conventionally used in injectable vehicles for administration of local anesthetics can also be present in the vehicle containing the anesthetic and the lithium ions in admixture or in one or more of the vehicle containing the anesthetic and the vehicle containing the lithium ions where the vehicles are separately prepared but used in combination to achieve the objects of the present invention.

The following examples are provided for illustrative purposes only, and are in no way intended to limit the scope of the present invention. Unless otherwise indicated all pans, percents, ratios and the like are by weight.

SYNTHESIS EXAMPLES

Synthesis Example 1:

Standard Buffer Vehicle

The standard buffer vehicle used as the control buffer vehicle in the Examples of the present invention was Locke's physiological saline. Hereinafter, this buffer vehicle is referred to as "sodium Lockes".

The sodium Lockes solution was prepared fresh in liter quantities with the following concentrations of reagents or stock solutions: 1.98 g of glucose, 34 ml of 4M NaCl, 5.6 ml of 1M KCl, 6 ml of 0.2M $NaH_2PO_4$, 28.6 ml of 0.5M $NaHCO_3$ and 1.2 ml of 1M $MgCl_2$.

These materials were QSed to 995 ml with distilled $H_2O$. The solution was bubbled for 5 minutes with 95% $O_2$/5% $CO_2$. Following bubbling, 2.2 ml of 1M $CaCl_2$ and 10 microliter of 3M choline chloride were added. The solution was adjusted to pH 7.3 with dilute HCl.

The local anesthetics were tested as molar concentrations dissolved in the above sodium Lockes solution.

Synthesis Example 2:

Lithium-Containing Buffer Vehicle

The lithium-containing buffer vehicle within the present invention used as the experimental vehicle in the Examples of the present invention was Lockes physiological saline, wherein 35% molar Eq. of the sodium ions had been replaced by lithium ions. Hereinafter, this buffer is referred to as "lithium Lockes".

The lithium Lockes solution was prepared fresh in liter quantities with the following concentrations of reagents or stock solutions: 1.98 g of glucose, 24 ml of 4M NaCl, 10 ml of 4M LiCl, 5.6 ml of 1M KCl, 6 ml of 0.5M $NaHCO_3$, 6 ml of 0.2M $NaH_2PO_4$, 54 ml of 0.1M $Li_2CO_3$ and 1.2 ml of 1 M $MgCl_2$.

These materials were QSed to 995 ml with distilled $H_2O$. The solution was bubbled for 5 minutes with 95% $O_2$/5% $CO_2$. Following bubbling, 2.2 ml of 1M $CaCl_2$ and 10 microliter of 3M choline chloride were added. The solutions was adjusted to pH 7.3 with dilute HCl.

The local anesthetics were tested as molar concentrations dissolved in the above lithium Lockes solution.

EXAMPLE 1

In Vitro Testing

To test if replacement of lithium ions for sodium ions reduced the required local anesthetic dose, an in vitro experiment was performed, wherein the electrically stimulated compound action potentials were recorded from desheathed ferret vagus nerves, which are an enriched source of C fibers.

A nerve chamber was used for the in vitro recording of action potentials. This nerve chamber was constructed at the University of Maryland at Baltimore. It was 9.5 cm long and 3.5 cm wide. Platinum commercial grade 0.020 inches diameter low resistance, corrosion resistant wire was used in the construction of the nerve chamber.

A central well having a 1 ml volume was provided to contain a wash buffer or a drug solution. The nerve was placed in the nerve chamber such that it passed over the stimulating electrodes, into the well and then over the recording electrodes. The well can be continuously perfused using a push/pull infusion system. The chamber was maintained at room temperature.

A computer based system was used to measure conduction velocity, magnitude of the action potential, area under the curve of the action potential and the rate of rise of the action potential (dV/dT), which is dependent upon the rate and magnitude of opening of voltage dependent $Na^+$ channels.

The system recorded compound action potential and derived the contributing frequencies and the characteristics of the wave forms in those frequencies. The computer archived data, perforated signal averaging, plotted derived wave forms, controlled stimulus parameters, and provided tabular and graphical results which were analyzed statistically.

Stimulus conditioning and signal pre-amplification was accomplished using a Grass S888 stimulator and a DAM80 preamplifier.

A Modular Instruments, Inc., data acquisition system was used. This system consisted of:

1. Hardware
    a. 100 mainframe, the physical box that the remainder of the acquisition system fits into. It included a power supply and foundation board, etc.
    b. M 202 fast A/D converter module, for input of the analog signals from the nerve and conversion of the signal to digital form to be used by the computer.
    c. M 212 pulse generator, controls the electro-physiological stimulator and contains a clock and has memory functions.
    d. M 210 memory buffer module, 24K×16 channels of input. Allows the fast acquisition rate required for electro-physiological data.
2. Software
    a. S 100 Run-Time Library utilities.
    b. S-225 Digascope, software to collect and analyze the action potentials.
    c. S-200 Signal Processing Package—FFT, area under curve, slope, and conduction velocity are calculated using cursors.
    d. S-211 Signal Average Package—Averages a specified number of successive action potentials.

The ferret vagus nerves were removed bilaterally and were desheathed under a Zeiss dissecting microscope with a magnification of 2.5X. A single desheathed nerve was then placed in a chamber interlaced with electrodes for stimulating and recording action potentials. The central section of the nerve passes through the central well containing either buffer or drug in buffer.

The stimulation voltage was adjusted to provide maximal action potential. The stimulus duration was 0.5 milliseconds. Stimulation and recording parameters were programmed, and stimuli were presented at 2 second intervals. Five successive action potentials were averaged and stored as an estimate of action potential activity each minute. The intervening twenty five action potential were discarded.

Control nerves were bathed in a 100% sodium Locke's solution, synthesized in the manner set forth in Synthesis Example 1 above. Experimental nerves were bathed in lithium Locke's solution, comprising 35 mol Eq. % lithium, 65 mol Eq. % sodium Locke's solution, synthesized in the manner set forth in Synthesis Example 2 above.

The electrical stimuli were applied to one end of the nerve, while on the other end, the resulting action potential propagation was measured using an oscilloscope and the recording computer. Varying doses of mepivacaine were administered to the nerves so that dose/response curves could be constructed under both ionic conditions.

Following a period of equilibration in a buffer where control recordings are made, the well was emptied and a molar concentration of a test anesthetic was added. Various molar concentrations of mepivacaine, an amide type local anesthetic (Sterling-Winthrop Research Institute, Rensselear, N.Y.), and procaine, an ester type local anesthetic (Sigma Chemical Co., St. Louis, Mo.) were tested in both sodium and lithium Locke's buffer vehicles, as described above.

Compound action potentials having two distinct peaks, labeled as A and C peaks, are observed and were recorded at 2 second intervals. Five consecutive action potentials were recorded for each one minute time period over 30 minutes. At 30 minutes, the anesthetic was removed and the chamber was perfused with buffer. Recording was continued during this 30 minute period. The averaged data, collected every 2 minutes, was then analyzed to determine the slope of the action potential, the height of the action potential, the area under the curve of the action potential and the conduction velocity. This was done for both the A and C peaks.

The data were then plotted as percent of control versus time. Other molar concentrations were administered from the dose where there was no effect on the A peak, and to a dose where the action potential was depressed to zero.

Inspection of the data allowed recording of the maximal observed effect for each of the concentrations studied. This observed maximum (or an asymptotic value derived from an appropriate equation) was used to generate log-probit linear regressions of the dose versus the effect. This is accomplished by conversion of the percent effect to the corresponding probit value, conversion of the dose to its log10 and fitting a first degree polynomial to the resultant data by the method of least squares.

The 95% confidence band was calculated and plotted for the data. From the equations of the best fit line and the confidence bands, doses estimated to produce 50, 90 and 95% depression of the four parameters were calculated for both the A and C peaks of the action potentials.

Rate of onset of drug effect can be calculated, for each parameter, by conversion of each time versus percent to a plot of time versus the percent maximal effect of the particular concentration using the equation

[((observed % depression—maximal % depression)/(100% depression—maximal % depression))*100].

Then the values between 95% and 5% of control are plotted versus time using the log of the percent. This provides a straight line and the time at which the parameter had reached 85% of its ultimate depression which was calculated from the regression line. These times were plotted versus the dose and the 50%, 90% and 95% depression doses substituted into the equation to calculate the time of 85% onset for each of the parameters for the A and C peaks.

Table 1 was prepared using the results of each of the concentrations onsets (T 85%). The estimated data for the dose producing a 50% ($ED_{50}$), 90% ($ED_{90}$) and 95% ($ED_{95}$) depression of the action potential voltage content are shown in Table 1 below.

As shown in Table 1, the $ED_{50}$ of mepivacaine was reduced from 0.42 millimolar to 0.27 millimolar in the lithium-containing buffer vehicle of the present invention. Similarly, the $ED_{50}$ of procaine was reduced from 0.54 millimolar to 0.19 millimolar in the lithium-containing buffer vehicle of the present invention.

The shift in the dose/response curve was not parallel and demonstrated that the effect of lithium was most pronounced at lower concentrations of mepivacaine and procaine (See FIGS. 1 to 4).

EXAMPLE 2

In Vivo Testing

To confirm the results of the in vitro experiments in vivo, an electrically stimulated tooth pulp pain model was used. The tooth pulps of the central incisors of rabbits were exposed using a high speed burr and dental drill. Using a template of central rabbit incisors to ensure uniformity, injections of mepivacaine with and without a 35% lithium Lockes solution within the present invention, were made bilaterally at the apex of the incisors.

Electrodes were inserted into the pulp chambers and the voltage required to elicit a lick/chew response was measured. The percentage analgesia was calculated from the following equation:

$$MPE=((TV-CV)/(10\ V-CV))\times 100$$

wherein TV is the voltage after treatment; CV is the control voltage, and 10 V are the maximum volts applied.

The percent analgesia was recorded 0, 5, 10, 15, 30, 60, 120 and 180 minutes after injection.

TABLE 1

| Anesthetic | $ED_{50}$ (95% confid.) millimolar | $ED_{90}$ (95% confid.) millimolar | $ED_{95}$ (95% confid.) millimolar |
|---|---|---|---|
| Mepivacaine in sodium Lockes | 0.42 (0.36–0.49) | 0.82 (0.68–1.06) | 1.00 (0.81–1.34) |
| Mepivacaine in lithium Lockes | 0.27 (0.17–0.37) | 0.80 (0.57–1.40) | 1.1 (0.74–2.20) |
| Procaine in sodium Lockes | 0.54 (0.45–0.64) | 0.98 (0.80–1.35) | 1.16 (0.92–1.70) |
| Procaine in lithium Lockes | 0.19 (0.12–0.26) | 0.62 (0.44–1.15) | 0.87 (0.58–1.90) |

TABLE 2

| Anesthetic | $ED_{50}$ (95% confid.) percent W/V | $ED_{90}$ (95% confid.) percent W/V | $ED_{95}$ (95% confid.) percent W/V |
|---|---|---|---|
| Mepivacaine in sodium Lockes | 1.92 (1.29–3.19) | 4.62 (2.88–13.31) | 5.91 (3.48–20.70) |
| Mepivacaine in lithium Lockes | 0.69 (0.44–0.99) | 2.70 (1.78–5.53) | 3.96 (2.45–9.76) |

Figure 5:
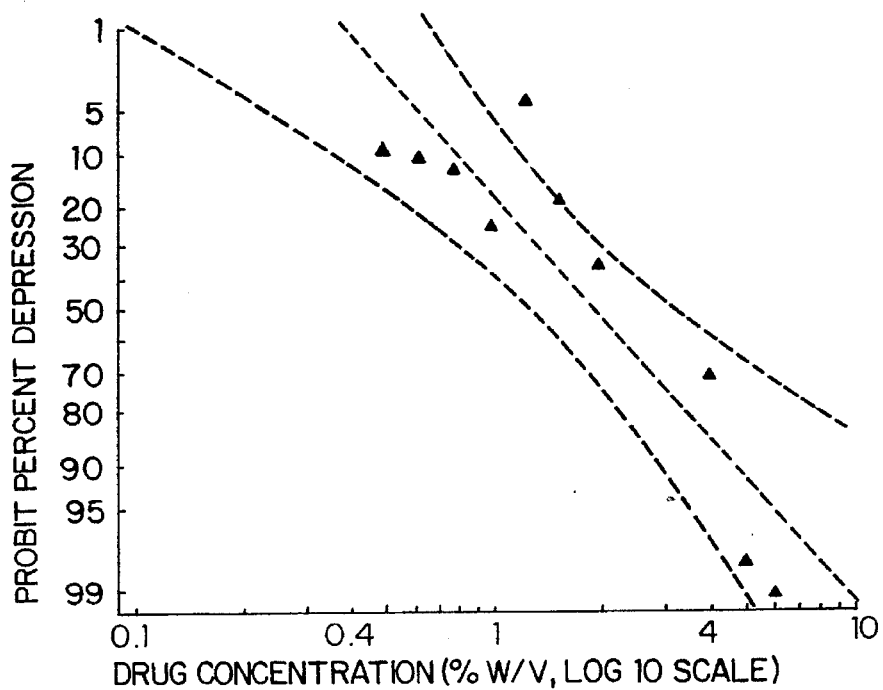
Figure 6:
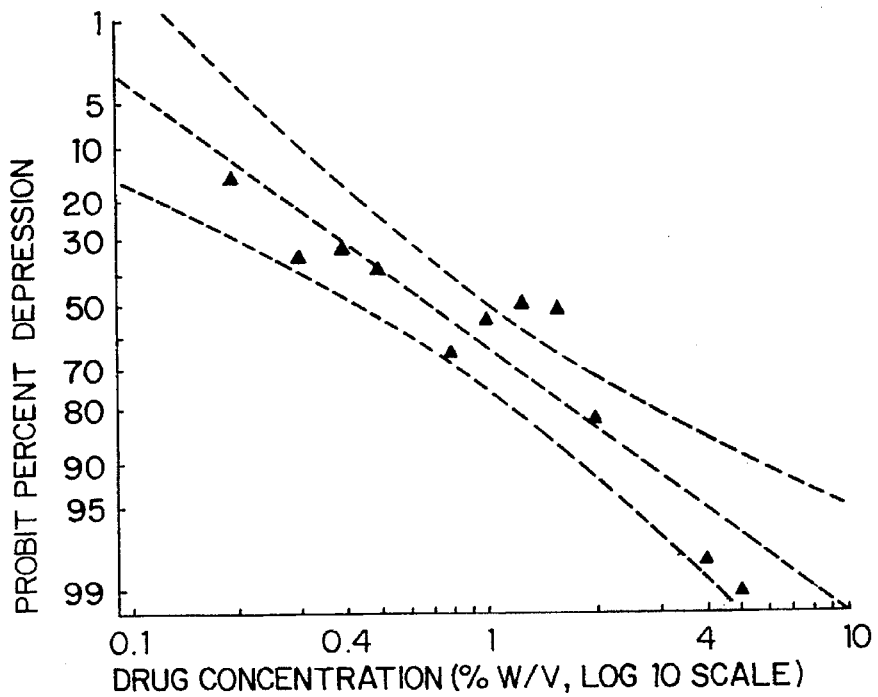

The results shown in Table 2 above demonstrate that the $ED_{50}$ of mepivacaine was reduced from 1.93% to 0.69% when lithium was present in the buffer vehicle. The shift in the dose/response curves was not parallel and demonstrated that the effect of lithium was most pronounced at lower concentrations of mepivacaine (see FIGS. 5 and 6).

As shown in the above Examples, the in vitro $ED_{50}$ dosages of mepivacaine and procaine were reduced to half their control values. The in vivo $ED_{50}$ of mepivacaine was reduced to one third of its value in the lithium Lockes buffer vehicle within the present invention, as compared to its value in the standard sodium Lockes vehicle. Thus, the lithium-containing buffer vehicle of the present invention induced $ED_{50}$ reduction of both mepivacaine and procaine due to ionic interference with the charge gradient, which reduced the flow of sodium through the voltage gated channels in nerve C fibers.

Accordingly, local anesthetics can be prepared in various percentage concentrations of lithium-containing buffer vehicles in accordance with the anaesthetic pharmaceutical combination of the present invention, wherein lithium ions have been substituted for sodium ions. By using the combination of the present invention including the lithium-containing buffer vehicle in accordance with the present invention, the doses of anesthetic will be significantly lowered, with the benefit of avoiding cardiac and central nervous system toxicity without compromising the depth of anesthesia for the patient. In addition, the combination of the present invention including lithium-containing vehicles in accordance with the present invention are particularly useful where repeated or high dose local anesthesia is required in medical procedures, such as hand surgery, obstetrics, bum therapy and dental restoration and extractions.

While the invention has been described in detail, and with reference to specific embodiments thereof, it will be apparent to one of ordinary skill in the art that various changes and modifications can be made therein without departing from the spirit and scope thereof.

What is claimed is:

1. An injectable pharmaceutical combination comprising (1) an effective amount of an anesthetic capable of providing a localized anesthetic characteristic and (2) an effective amount of lithium ions to reduce the amount of anesthetic required for equivalent pain sensation reduction.

2. The injectable anesthetic pharmaceutical combination of claim 1, wherein the anesthetic is selected from the group consisting of amide local anesthetics, ester local anesthetics, and antihistaminic anesthetics.

3. The injectable anesthetic pharmaceutical combination of claim 2, wherein said anesthetic is selected from the group consisting of lidocaine, bupivacaine, chloroprocaine, mepivacaine, procaine, tetracaine, etidocaine and mixtures of two or more thereof.

4. The injectable anesthetic pharmaceutical combination of claim 1, wherein the amount of lithium ions is equivalent to an amount of 10 to 90 mmolar when administered in solution.

5. The injectable anesthetic pharmaceutical combination of claim 4, wherein the amount of lithium ions is equivalent to an amount of 35 to 65 mmolar when administered in solution.

6. The injectable anesthetic pharmaceutical combination of claim 1, wherein the combination comprises a sodium ion and lithium ion containing vehicle and the molar ratio of lithium ions to sodium ions is 2:1 to 1:2.

7. The injectable anesthetic pharmaceutical combination of claim 1, wherein said combination comprises an injectable vehicle comprising said local anesthetic and said lithium ions in admixture.

8. The injectable anesthetic pharmaceutical combination of claim 1, wherein said vehicle comprises an injectable physiologically acceptable vehicle containing said anesthetic and said lithium ions and additionally contains one or more additional physiologically acceptable agents selected from the group consisting of sodium ions sufficient for body fluid isotonicity, a buffering agent for pH adjustment and control, a vasoconstrictor, an antioxidant, a preservative and a stabilizing agent.

9. A method for enhancing localized anesthetic effect upon administration of a local anesthetic to a human or animal patient comprising administering to said human or animal patient by injection (1) an effective amount of an anesthetic capable of providing a localized anesthetic characteristic and (2) an effective amount of lithium ions to reduce the amount of anesthetic required for equivalent pain sensation reduction.

10. The method recited in claim 9, wherein the anesthetic is selected from the group consisting of amide local anesthetics, ester local anesthetics, and antihistaminic anesthetics.

11. The method recited in claim 10, wherein said anesthetic is selected from the group consisting of lidocaine, bupivacaine, chloroprocaine, mepivacaine, procaine, tetracaine, etidocaine and mixtures of two or more thereof.

12. The method recited in claim 9, wherein the amount of lithium ions is equivalent to an amount of 10 to 90 mmolar when administered in solution.

13. The method recited in claim 9, wherein the amount of lithium ions is equivalent to an amount of 35 to 65 mmolar when administered in solution.

14. The method recited in claim 9, wherein the combination comprises a sodium ion and lithium ion containing vehicle and the molar ratio of lithium ions to sodium ions is 2:1 to 1:2.

15. The method recited in claim 9, wherein said combination comprises an injectable vehicle comprising said local anesthetic and said lithium ions in admixture.

16. The method recited in claim 9, wherein said vehicle comprises an injectable physiologically acceptable vehicle containing said local anesthetic and said lithium ions and additionally contains one or more additional physiologically acceptable agents selected from the group consisting of sodium ions sufficient for body fluid isotonicity, a buffering agent for pH adjustment and control, a vasoconstrictor, an antioxidant, a preservative and a stabilizing agent.

* * * * *